United States Patent
Crotty et al.

(10) Patent No.: US 10,368,825 B2
(45) Date of Patent: Aug. 6, 2019

(54) METHODS AND SYSTEMS FOR COMPUTED TOMOGRAPHY

(71) Applicant: General Electric Company, Schenectady, NY (US)

(72) Inventors: Dominic Joseph Crotty, Waukesha, WI (US); Roy A. Nilsen, Waukesha, WI (US); Jiahua Fan, New Berlin, WI (US); Mary Sue Kulpins, Brookfield, WI (US); Franco Rupcich, Wauwatosa, WI (US); Grant Morey Stevens, Kaysville, UT (US)

(73) Assignee: General Electric Company, Schenectady, NY (US)

( * ) Notice: Subject to any disclaimer, the term of this patent is extended or adjusted under 35 U.S.C. 154(b) by 652 days.

(21) Appl. No.: 15/002,122

(22) Filed: Jan. 20, 2016

(65) Prior Publication Data

US 2017/0202534 A1    Jul. 20, 2017

(51) Int. Cl.
*A61B 6/00* (2006.01)
*A61B 6/03* (2006.01)

(52) U.S. Cl.
CPC ............. *A61B 6/542* (2013.01); *A61B 6/032* (2013.01); *A61B 6/465* (2013.01); *A61B 6/488* (2013.01); *A61B 6/5205* (2013.01); *A61B 6/544* (2013.01); *A61B 6/467* (2013.01)

(58) Field of Classification Search
CPC ......... A61B 6/032; A61B 6/465; A61B 6/488; A61B 6/542; A61B 6/544; A61B 6/582; A61B 6/583
See application file for complete search history.

(56) References Cited

U.S. PATENT DOCUMENTS

| | | | | |
|---|---|---|---|---|
| 2006/0193437 A1* | 8/2006 | Boeing | ................... | A61B 6/032 378/115 |
| 2013/0101079 A1* | 4/2013 | Hough | ..................... | A61B 6/03 378/8 |
| 2013/0148784 A1* | 6/2013 | Tajima | ..................... | H05G 1/42 378/62 |
| 2014/0270053 A1 | 9/2014 | Larson | | |

FOREIGN PATENT DOCUMENTS

WO    2013049818 A1    4/2013

OTHER PUBLICATIONS

Boone, J. et al., "Size-Specific Dose Estimates (SSDE) in Pediatric and Adult Body CT Examinations," AAPM Report No. 204, Available as Early as Jan. 2011, College Park, MD, 30 pages.
McCollough, C. et al., "Use of Water Equivalent Diameter for Calculating Patient Size and Size-Specific Dose Estimates (SSDE) in CT," AAPM Report No. 220, Sep. 2014, College Park, MD, 23 pages.

* cited by examiner

Primary Examiner — Chih-Cheng Kao
(74) Attorney, Agent, or Firm — McCoy Russell LLP (57) ABSTRACT

Methods and systems are provided for automatic exposure control in computed tomography imaging systems. In one embodiment, a method comprises in response to an object-specific dose metric input by a user via a user interface operably coupled to a scanner, predicting an image quality of a diagnostic scan, calculating an output level of a source of the scanner for the image quality, and performing the diagnostic scan at the output level when the image quality is higher than a threshold. In this way, patient-specific image quality settings may be determined.

20 Claims, 6 Drawing Sheets

METHODS AND SYSTEMS FOR COMPUTED TOMOGRAPHY

FIELD

Embodiments of the subject matter disclosed herein relate to non-invasive diagnostic imaging, and more particularly, to automatic exposure control in computed tomography imaging systems.

BACKGROUND

Non-invasive imaging technologies allow images of the internal structures of a patient or object to be obtained without performing an invasive procedure on the patient or object. In particular, technologies such as computed tomography (CT) use various physical principals, such as the differential transmission of x-rays through the target volume, to acquire image data and to construct tomographic images (e.g., three-dimensional representations of the interior of the human body or of other imaged structures).

Modern CT systems include automatic exposure control (AEC) configured to set the dose operating point to achieve optimized performance between image quality and radiation dose. Radiation exposure from CT scanners is measured in terms of the volumetric CT Dose Index (CTDIvol). Although governed by the size of the patient anatomy, the CTDIvol metric does not consider patient size, and so CTDIvol is related to x-ray tube output, as determined by the employed scanning technique, rather than individual patient size.

In an effort to create a practicable and patient-centered dose metric, a Task Group from the American Association of Physicists in Medicine (AAPM TG #204) proposed using an improved patient size-specific dose metric that modifies the CTDIvol of scan with reference to estimated patient size; this size-specific dose estimate (SSDE) metric (a metric related to the patient's attenuation and size) has been found to be an improved surrogate for actual patient absorbed dose, when compared to CTDIvol. Current embodiments of the SSDE metric are determined after scan data is acquired by calculating dimensions from tomographic axial images, i.e. the effective patient diameter Deff. Since the Deff is currently derived from reconstructed axial images of the patient, the SSDE is a post hoc dose metric and cannot govern the a priori patient exposure for a clinical imaging task.

BRIEF DESCRIPTION

In one embodiment, a method comprises, in response to receiving an object-specific dose metric input by a user via an interface operably coupled to a scanner, predicting an image quality of a diagnostic scan, calculating an output source exposure level of the scanner for the predicted image quality, and performing the diagnostic scan at the specified output source exposure level responsive to the image quality above a threshold. In this way, the user may be able to input a dose specific to the patient, thereby governing the output level of the x-ray source that appropriately exposes the patient for a given clinical imaging task.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 4:
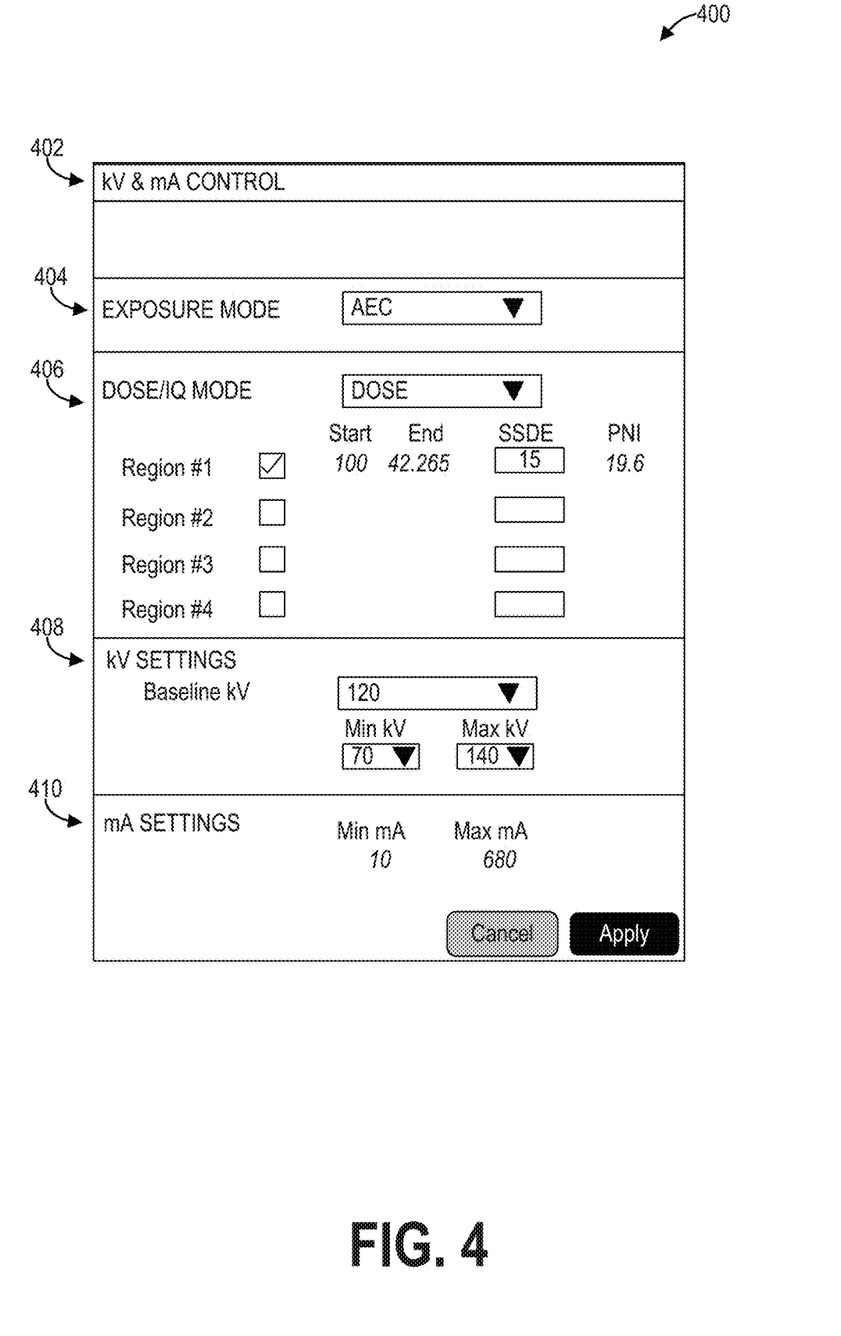
FIG. 4 shows an exemplary user interface of the AEC module.
Figure 5:
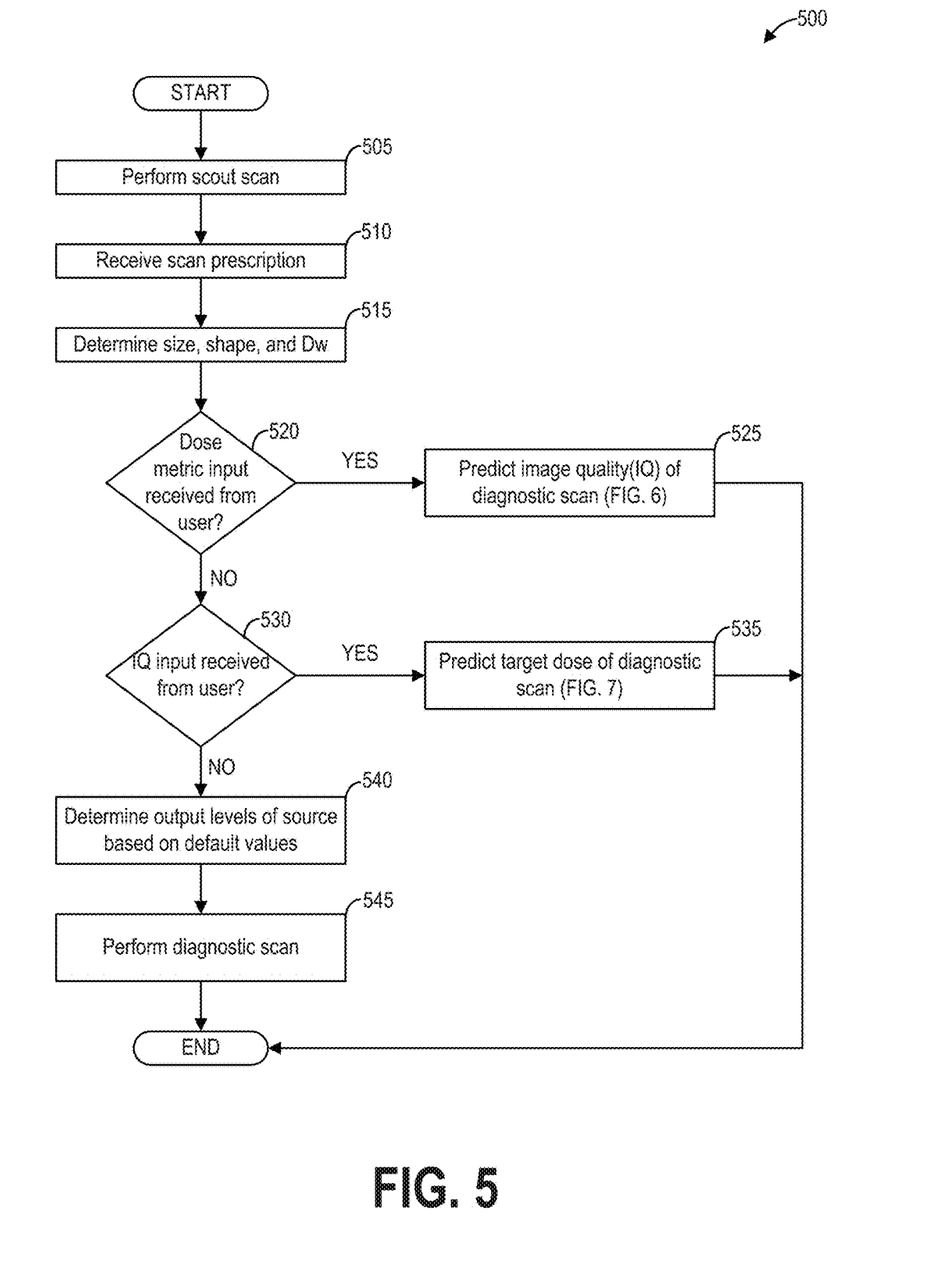
FIG. 5 shows a high-level flow chart illustrating an example method for receiving a dose metric input or an image quality input via the interface of the AEC module.

The following description relates to various embodiments of medical imaging systems. In particular, methods and systems are provided for automatic exposure control. An example of a computed tomography (CT) imaging system that may be used to acquire images processed in accordance with the present techniques is provided in FIGS. 1 and 2. CT systems may include an automatic exposure control (AEC) feature described in FIG. 3, wherein the output level of the source may be adjusted based on one of a user-prescribed dose input or image quality input (FIG. 5). Herein, a user may prescribe patient-specific dose metric input or an image quality input via a user interface as shown in FIG. 4. When a dose metric input is received, a method shown in FIG. 6, may include determining parameters of a diagnostic scan based on the dose metric input received, and further predicting an image quality of the diagnostic scan based on the dose metric input. Likewise, when an image quality input is received, a method shown in FIG. 7, may include determining the parameters of the diagnostic scan based on the image quality input received, and further predicting a target dose of the diagnostic scan based on the dose metric input. As part of the AEC methodology, an initial estimation of patient size is commonly generated by the CT system prior to diagnostic scan portion of the patient exam. Thus a patient size specific estimate of dose, such as SSDE, may be predicted for the prescribed exam by combining this estimated patient size and other information contained within the scan prescription. Furthermore, this prediction of patient specific dose may be used to enable prescription of the scan.

Though a CT system is described by way of example, it should be understood that the present techniques may also be useful when applied to images acquired using other imaging modalities, such as tomosynthesis, C-arm angiography, and so forth. The present discussion of a CT imaging modality is provided merely as an example of one suitable imaging modality.

As used herein, the phrase "pixel" also includes embodiments of the invention where the data is represented by a "voxel." Thus, both the terms "pixel" and "voxel" may be used interchangeably herein.

Also as used herein, the phrase "reconstructing an image" is not intended to exclude embodiments of the present invention in which data representing an image is generated, but a viewable image is not. Therefore, as used herein, the term "image" broadly refers to both viewable images and data representing a viewable image. However, many embodiments generate (or are configured to generate) at least one viewable image.

Various embodiments may be implemented in connection with different types of imaging systems. For example, various embodiments may be implemented in connection with a CT imaging system in which an x-ray source projects a fan- or cone-shaped beam that is collimated to lie within an x-y plane of a Cartesian coordinate system and generally referred to as an "imaging plane." The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurement from all the detectors is acquired separately to produce a transmission profile.

In third-generation CT systems, the x-ray source and the detector array are rotated with a gantry within the imaging plane and around the object to be imaged such that the angle at which the x-ray beam intersects the object constantly changes. A complete gantry rotation occurs when the gantry concludes one full 360 degree revolution. A group of x-ray attenuation measurements (e.g., projection data) from the detector array at one gantry angle is referred to as a "view." A view is, therefore, each incremental position of the gantry. A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as a filtered backprojection technique. This process converts the attenuation measurements from a scan into integers called "CT numbers" or "Hounsfield units" (HU), which are used to control the brightness of a corresponding pixel on, for example, a cathode ray tube display.

Figure 1:
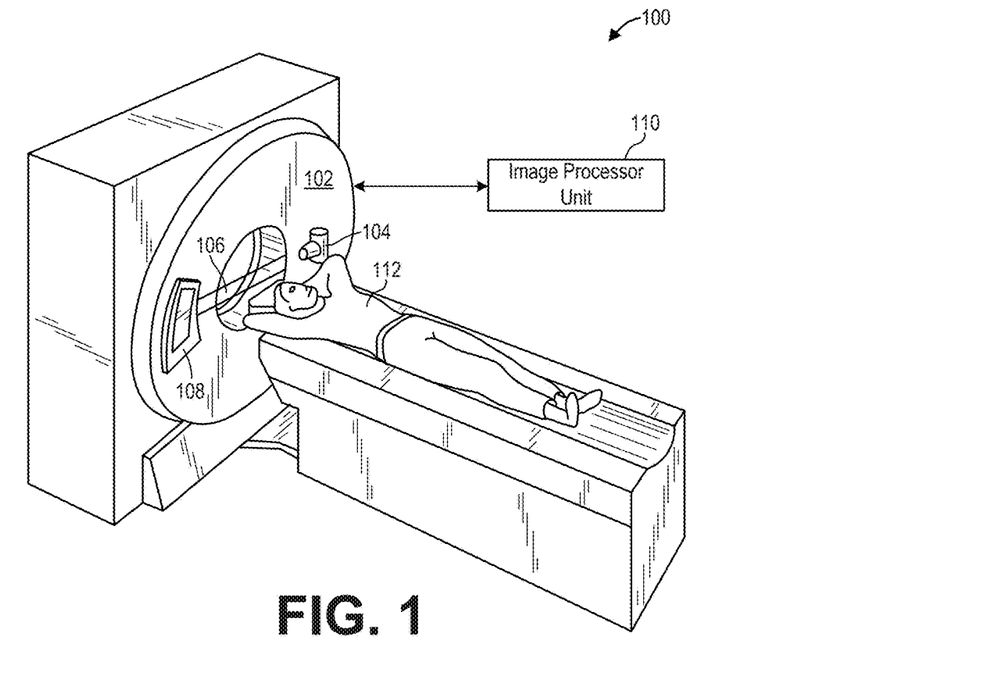
FIG. 1 shows a pictorial view of an imaging system according to an embodiment of the invention.

FIG. 1 illustrates an exemplary CT system 100 configured to allow fast and iterative image reconstruction. Particularly, the CT system 100 is configured to image a subject such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 for use in imaging the patient. Specifically, the radiation source 104 is configured to project the x-rays 106 towards a detector array 108 positioned on the opposite side of the gantry 102. Although FIG. 1 depicts only a single radiation source 104, in certain embodiments, multiple radiation sources may be employed to project a plurality of x-rays 106 for acquiring projection data corresponding to the patient at different energy levels.

In certain embodiments, the CT system 100 further includes an image processing unit 110 configured to reconstruct images of a target volume of the patient using an iterative or analytic image reconstruction method. For example, the image processing unit 110 may use an analytic image reconstruction approach such as filtered backprojection (FBP) to reconstruct images of a target volume of the patient. As another example, the image processing unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the patient.

Figure 2:
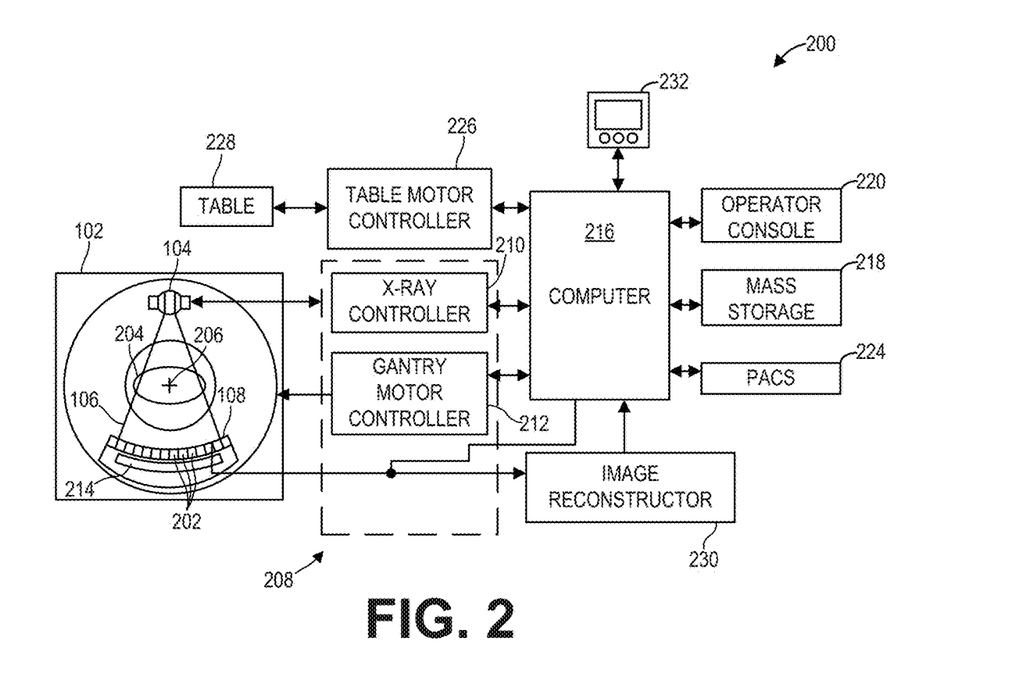
FIG. 2 shows a block schematic diagram of an exemplary imaging system according to an embodiment of the invention.

FIG. 2 illustrates an exemplary imaging system 200 similar to the CT system 100 of FIG. 1. In accordance with aspects of the present disclosure, the system 200 is configured to perform automatic exposure control responsive to user input. In one embodiment, the system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device (also referred to as processor) 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes, or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a motorized table 228. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely, and may be operatively connected to the system 100 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

Figure 3:
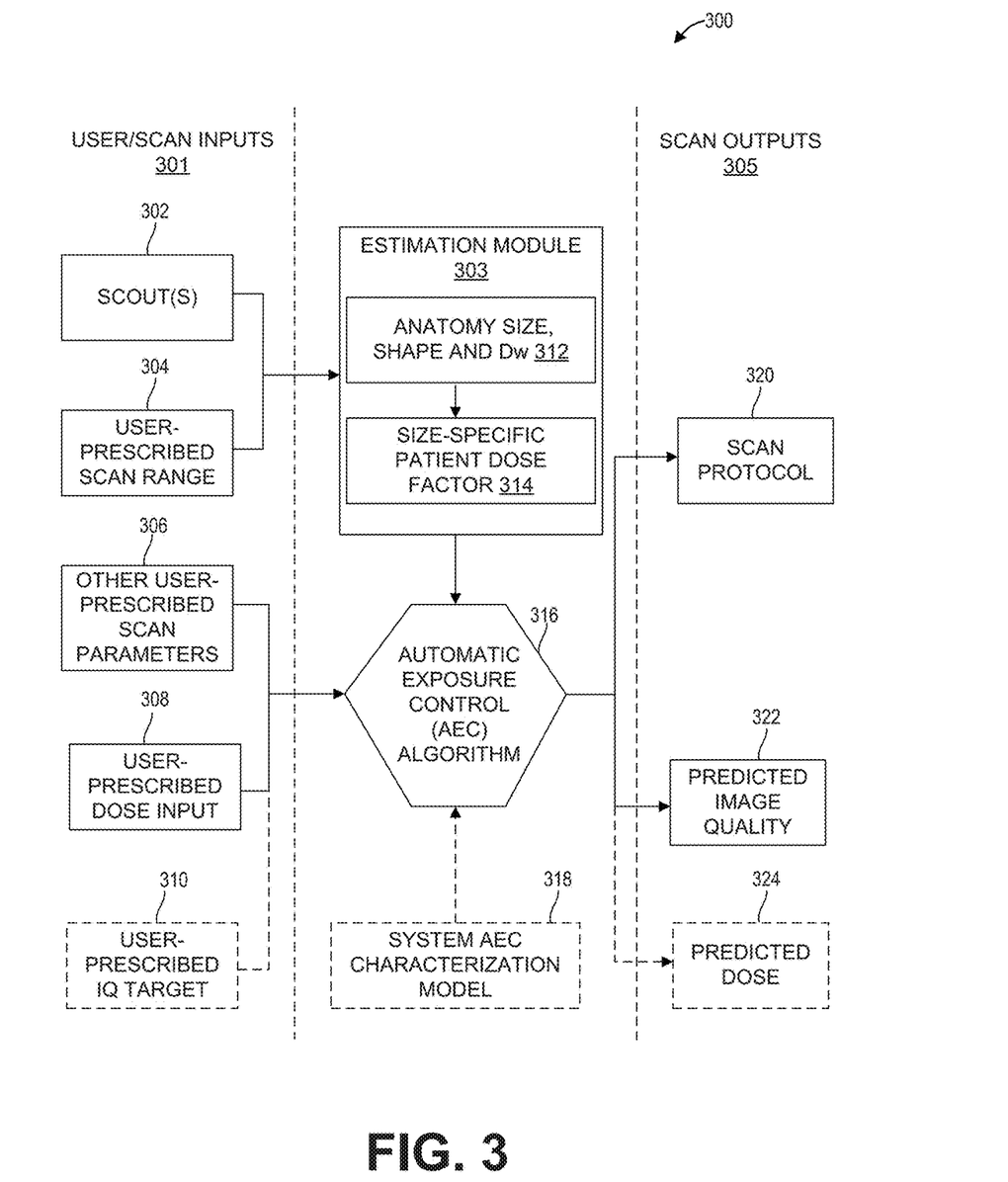
FIG. 3 shows a block schematic diagram of an exemplary automatic exposure control (AEC) module.

In certain embodiments, the computing device 216 may include an automatic exposure control (AEC) module 300 shown in FIG. 3 that may govern the level of patient exposure or patient dose of radiation from a source of the CT scanner, such as an x-ray source for example. In some embodiments, the AEC module may be an independent module, separate from and communicatively coupled to the computing device 216 of FIG. 2. In other embodiments, the AEC module 300 may be integrated within the computing device 216.

Turning to FIG. 3, a block schematic diagram of an automatic AEC module 300 is shown. The AEC module 300 may include user/scan inputs 301 input into an AEC algorithm 316, and the AEC algorithm 316 may determine scan outputs 305 based on the user/scan inputs 301 to determine patient-specific dose, for example.

As explained earlier, radiation exposure from CT systems may be measured in terms of the volumetric CT Dose Index (CTDIvol). As such, the CTDIvol was developed to provide a standardized method to compare radiation output levels between different CT scanners using a reference phantom. Dose length product (DLP), which is the product of CTDIvol and scan length, may give a measure of the total ionizing energy imparted to the reference phantom. However, both CTDIvol and DLP are independent of patient size. Typically, the CTDIvol is determined for either a 16 cm or 32 cm diameter reference phantom. For example, for scanning a head of a patient, the 16 cm diameter phantom is used, and for scanning a torso of the patient, the 32 cm diameter phantom is used.

Since the CTDIvol is related to scanner output and not to patient size, the CTDIvol may not give a measure of patient dose, for example. However, based on a scout scan, it may be possible to calculate a size-specific dose factor, for example, as discussed below.

The AEC module 300 may be configured to determine the scan parameters to achieve optimal performance between image quality and radiation dose. Certain scanning parameters, such as x-ray tube current ("mA"), x-ray tube supply voltage ("kV"), slice thickness, scan time, and helical pitch (for helical scans) are known to affect the scan power, which in turn affects image quality. In addition, the x-ray tube current typically directly relates to the patient x-ray dose. A higher x-ray tube current may, for example, improve the image quality but increase the dosage received by the patient. However, lower x-ray tube current levels are known to cause severe streaking artifacts in the image.

User/scan inputs 301 may encompass both user-specified inputs and scan inputs. Herein, user specified inputs may include user-prescribed scan range 304, user-prescribed dose input 308, user-prescribed image quality target 310 and other user prescribed scan parameters 306. Scan inputs may include one or more scout scans 302 performed on the patient/object.

Scout scan(s) 302 may comprise a preliminary scan performed on a patient or object using a CT system with a reduced dosage. Further, scout scans of a patient anatomy may be acquired prior to a diagnostic scan. User-prescribed scan range 304 may include a scan prescription such as scan length or duration, scan region, and the like. The scout scans 302 and the user-prescribed scan range 304 may be inputs to an estimation module 303, wherein patient specific estimates may be deduced as described below.

The estimation module 303 may calculate anatomy size, shape and water equivalent diameter Dw at 312 based on the scout scan 302 and user-prescribed scan range 304. X-ray attenuation of a patient may be expressed in terms of water cylinder having the same x-ray attenuation. Herein, Dw is the diameter of such a cylinder. Further, at 314, the estimation module 303 may estimate a size-specific patient dose factor. As such, the estimation module may be a model such as an algorithmic model, simulation model, and the like. In some examples, the estimation module may be a database, look-up table, surface map, and the like. In some examples, the size-specific dose factor may be determined from size-specific dose factor models or from published literature, from internal system characterization models (empirically-based or analytical), or from models developed and/or specified by the user. In this way, by calculating the SSDE based on a scout-generated Dw, for example, this patient-specific and patient-size related input dose metric can be prescribed by the user prior to the scan, thus governing the x-ray tube output that appropriately exposes the patient for a given clinical imaging task.

The AEC module 300 may further include user-prescribed dose input 308, and user-prescribed image quality (IQ) target. The user may enter an IQ metric (which may comprise, as a non-limiting example, a Noise Index (NI)) or a dose metric (which may comprise, as a non-limiting example, Size Specific Dose Estimate (SSDE)) to govern the operation of an AEC protocol. As such, the image quality metric may be manually or automatically determined, based on the clinical indication of the study or the image quality of a prior study, for example. As explained earlier, the CTDIvol may be known a priori. By using the CTDIvol information known a priori, the AEC algorithm 316 may be able to determine specific dose levels to be applied to the patient. Using the SSDE-based dose target as an example: by calculating the SSDE based on a scout-generated Dw, this patient-specific and patient-size related input dose metric can be prescribed by the user prior to the scan, thus governing the x-ray tube output that appropriately exposes the patient for a given clinical imaging task.

As such, the user-prescribed IQ target, may be described in terms of contrast, spatial resolution, noise index, artifacts, and the like. The user-prescribed dose input 310 may be described in terms of SSDE, for example. In some embodiments, look-up tables or databases including variation in dose or CTDIvol, or a derivative thereof, as a function of input x-ray tube exposure, may be maintained in the system AEC characterization model 318. Similarly, look-up tables or databases including variation in output image quality (such as NI) as a function of input dose or SSDE (or derivative thereof) may also be maintained as the system AEC characterization model 318. The AEC characterization model 318 may characterize the IQ performance of the CT system in response to varying x-ray technique parameters (including but not limited to kV, mA) and as a function of patient size. For example, the model may take the form of a single master AEC model, based on a pre-defined set of x-ray technique parameters, with derivatives of the master model determined from known IQ performance variation as a function of x-ray technique variation and patient anatomy size. In an example embodiment, the AEC characterization model may be a model specific to individual sets of input x-ray technique parameters. In another example embodiment, the model dose to IQ AEC model may be user-specified. The output IQ performance of the system may be predicted from the input x-ray exposure, and with patient dose similarly estimated from the input exposure a single AEC model that predicts IQ as a function of patient dose may be created.

In some embodiments, other user-prescribed scan parameters such as scan length, anatomical region being scanned and the like, may be included in other user-prescribed scan parameters 306, and may be input into the AEC algorithm 316. As such, the AEC algorithm 316 may use the size information of the anatomical region being scanned, in addition to the user-prescribed image quality or patient dose target, to calculate an appropriate level of exposure for the scan and output it to scan protocol 320. Further, based on the user-prescribed dose input, the AEC algorithm may adaptively look up and/or predict a dose 324. Likewise, based on a user-prescribed IQ target for a patient-size dose input 308, the AEC algorithm 316 may look up and/or predict target dose 324. In some examples, based on dose input, a first x-ray tube exposure based on the dose input may be determined by the AEC module, and further a second x-ray tube exposure based on one or more of a clinical range selection, an object size, an object shape and a water-equivalent diameter may be predicted. In such examples, a diagnostic scan may be performed when a difference between the first x-ray tube exposure and the second x-ray tube exposure is lower than a threshold. Likewise, based on an image quality input a first dose metric based on the image quality input may be determined by the AEC module, and further a second dose metric based on one or more of the clinical range selection, the object size, the object shape and the water equivalent diameter may be predicted. Herein, the diagnostic scan may be performed when difference between the first dose metric and the second does metric is lower than a threshold.

In this way, the AEC algorithm may use the estimated patient size (Dw) and a target IQ or input dose (SSDE) to generate a patient-specific dose or IQ, for example.

The user-prescribed dose input 308 and the user-prescribed IQ target 310 may be entered via a user interface of the AEC module of the CT system. FIG. 4 shows an example user interface 400 for a CT system for providing user input for automatic exposure control. For example, user interface 400 may be displayed on the display 232 communicatively coupled to the computing device 216 and/or the image reconstructor 230 of FIG. 2. In some embodiments, the display 232 may be operably coupled to the AEC module 300 of FIG. 3. The user interface 400 may accept input from a user (e.g., touch input provided to the display). The user interface 400 may include a display 402 for kV and mA control of the x-ray source. As explained earlier, scanning parameters, x-ray tube supply voltage ("kV"), and such as x-ray tube current ("mA"), and the like, may affect the image quality of the scan, for example.

The display 402 may further include one or more sections, such as section 404, 406, 408, and 410, which may be displayed simultaneously on the same screen. In other examples, one or more of the sections may be displayed on separate screens between which the user may navigate. For example, sections 404 and 406 may be displayed on a first screen while sections 408 and 410 may be displayed on a second separate screen, and the user may navigate between the first and the second screens. The section 404 may allow the user to select the exposure mode. For example, the user may be able to select AEC, indicating that the user wishes the exposure and dose be determined automatically using the automatic exposure control features discussed earlier with reference to FIG. 3.

In section 406 of the user interface 400, the user may be have the option of selecting either a dose input or an IQ target. In the depicted example, the user may prescribe a range of clinically acceptable values for the dose metric or that image quality metric. When "DOSE" input is selected in section 406 of the user interface 400, the user may be able to enter a value of SSDE input, for example. In some examples, the user may not necessarily specify that the user is using the "DOSE" method. For example, it should be appreciated that in some examples the user may select a dose input or an IQ target without first specifying a particular mode (e.g., "DOSE" or "IQ"). Based on the dose value entered, the AEC algorithm may be able to predict an IQ (predicted noise input, PNI, for example). The user may additionally be able to select a scan region (say region #1, for example) and further prescribe a scan range by entering range into Start and End portions of the section 406. In other examples, the user may interact with the user interface and specify graphically via the UI the desired target for the specified scan region. As such, the desired target may be the dose or the IQ metric. In some examples, the user may be able to specify more than one scan region. Further, based on the scan range, anatomical region to be scanned, patient size and shape (as determined from the scout scan), the AEC algorithm may be able to determine scan parameters of the scan protocol such as kV (section 408) and mA (section 410) settings. Herein, the kV setting refers to the voltage applied to the x-ray source, and adjusting the kV setting based on an input dose adjusts the dose specific to the patient. In some embodiments, the user may be able to set minimum and maximum limits of voltage that is applied to the x-ray source by inputting values into the Min kV and Max kV selections in section 408. Similar limits may be set to the current (mA) settings in section 410.

In a similar way, the user may be able to choose IQ input in section 406. Based on the IQ value entered, the AEC algorithm may be able to predict a dose and accordingly adjust one or more of the voltage and the current applied to the x-ray source, and the exposure time of the x-ray source or adjust other prescribed parameters (such as rotation time, scan length, scan field of view, and the like) to adjust the patient dose.

It should be understood that the illustrated user interface elements are exemplary in nature, and any suitable interface for controlling the various AEC settings may be provided in any suitable configuration. For example, where buttons are shown, other actuatable elements such as sliders, knobs, menus, text boxes, and/or other user interface elements for accepting user input may be included. Furthermore, although the illustrated example provides a displayed user interface, it is to be understood that one or more of the adjustment mechanisms may be associated with a hardware input device. For example, a slider of the user interface may be actuated by touching the slider bar and/or moving a finger along the slider bar and/or may be actuated by rotating a physical knob or pressing an up/down button to adjust the associated setting. The user interface elements for requesting adjustments to AEC module may be actuatable to request continuously variable adjustments between a maximum and minimum value (e.g., adjustments that are not limited to discrete levels and/or adjustments that are adjustable to an integer or decimal value).

The computer and/or the AEC module may translate the settings adjustments made via the input to the user interface into control commands that may be transmitted to the x-ray controller to effect the requested source voltage and/or current adjustments.

Thus, an example CT system comprises an x-ray source that emits a beam of x-rays toward an object to be imaged, an automatic exposure control (AEC) module operably connected to the source, and a processor operably coupled to the AEC module and configured with instructions in non-transitory memory that when executed cause the processor to receive a dose input from a user via a user interface communicatively coupled to the AEC module and look up a first x-ray tube exposure based on the dose input, and predict a second x-ray tube exposure based on one or more of a clinical range selection, an object size, an object shape and a water equivalent diameter. Additionally or alternatively, the processor may include further instructions for performing a diagnostic scan when a difference between the first x-ray tube exposure and the second x-ray tube exposure is lower than a threshold. Additionally or alternatively, the processor may be further configured to receive an image quality input from the user via the user interface of the AEC module and look up a first dose metric based on the image quality input, predict a second dose metric based on one or more of the clinical range selection, the object size, the object shape and the water equivalent diameter, and perform the diagnostic scan when difference between the first dose metric and the second does metric is lower than a threshold. As such, the image quality metric may be based on the clinical indication of the study or a prior study. Additionally or alternatively, the clinical range selection may include a scan length, and an anatomical region being scanned. Additionally or alternatively, each of the object size, the object shape and the water equivalent diameter may be determined based on a scout scan performed on the object.

Turning to FIG. 5, it illustrates an example method for receiving a dose metric input or an image quality input via the interface of the AEC module. Specifically, based on the type of user input received via a user interface, the method adjusts automatic exposure control to govern patient-specific dose exposure.

Method 500 may be described with regard to the components and systems depicted in FIGS. 1-3, however it should be appreciated that the method may be applied to other components and systems without departing from the scope of the present disclosure. For example, method 500 (and methods 600 and 700 described here within) may be carried out by a computing device or processor, including but not limited to one or more of computing device or processor 216 and AEC module 300, and may be stored as executable instructions in non-transitory memory of the processor or computing device 216 and/or AEC module 300.

Method 500 may begin at 505. At 505, method 500 may include performing scout scan. Performing scout scan comprises performing a preliminary scan with a reduced dosage. Method 500 then proceeds to 510 where a scan prescription may be received. Scan prescription may include scan length, an indication of an anatomical region to be scanned, and the like. Next, method proceeds to 515, where patient size, shape and Dw metrics are calculated from the scout scan and the scan prescription.

Next, method 500 proceeds to 520, where it may be determined if a dose metric input is received from the user. As such, the dose metric input may be a user-prescribed dose input that the user may specify via a user interface (such as the user interface 400 of FIG. 4). A non-limiting example of a dose metric input may include user-specified size-specific dose estimate. If a dose metric input is received at 520, then method 500 proceeds to 525 where an image quality of the diagnostic scan may be predicted by performing a method 600 described with reference to FIG. 6, and method 500 ends.

However, if a dose metric input is not specified at 520, then method 500 proceeds to 530 where it may be determined if an image quality (IQ) input is received from the user. As such, the image quality input may be a user-prescribed IQ target and may include a noise index, for example, and may be entered via the user interface as explained earlier. If an IQ input is received at 530, then method 500 proceeds to 535 where a target dose of the diagnostic scan may be predicted by performing a method 700 described with reference to FIG. 7, and method 500 ends.

Thus, an example method for automatic exposure control, comprising deriving a level of exposure of an x-ray source of a scanner for a diagnostic scan using patient information and information of an anatomical region being scanned, and further adjusting the level of exposure based on a user-prescribed input entered by a user using an user interface operably coupled to the scanner, the input being one of a desired image quality and a desired dose target. Additionally or alternatively, the adjusting may further include calculating an output dose target based on one or more of the desired image quality, a volume computed tomography dose index, and a water-equivalent diameter. Additionally or alternatively, the adjusting may further include displaying the output dose target on the user interface, and performing the diagnostic scan when the output dose target is within a threshold dose. Additionally or alternatively, the method may include calculating an output image quality based on one or more of the desired dose target, a volume computed tomography dose index, and a water-equivalent diameter. Additionally or alternatively, the method may include displaying the output image quality on the user interface, and performing the diagnostic scan when the output image quality is within a threshold level.

Figure 6:
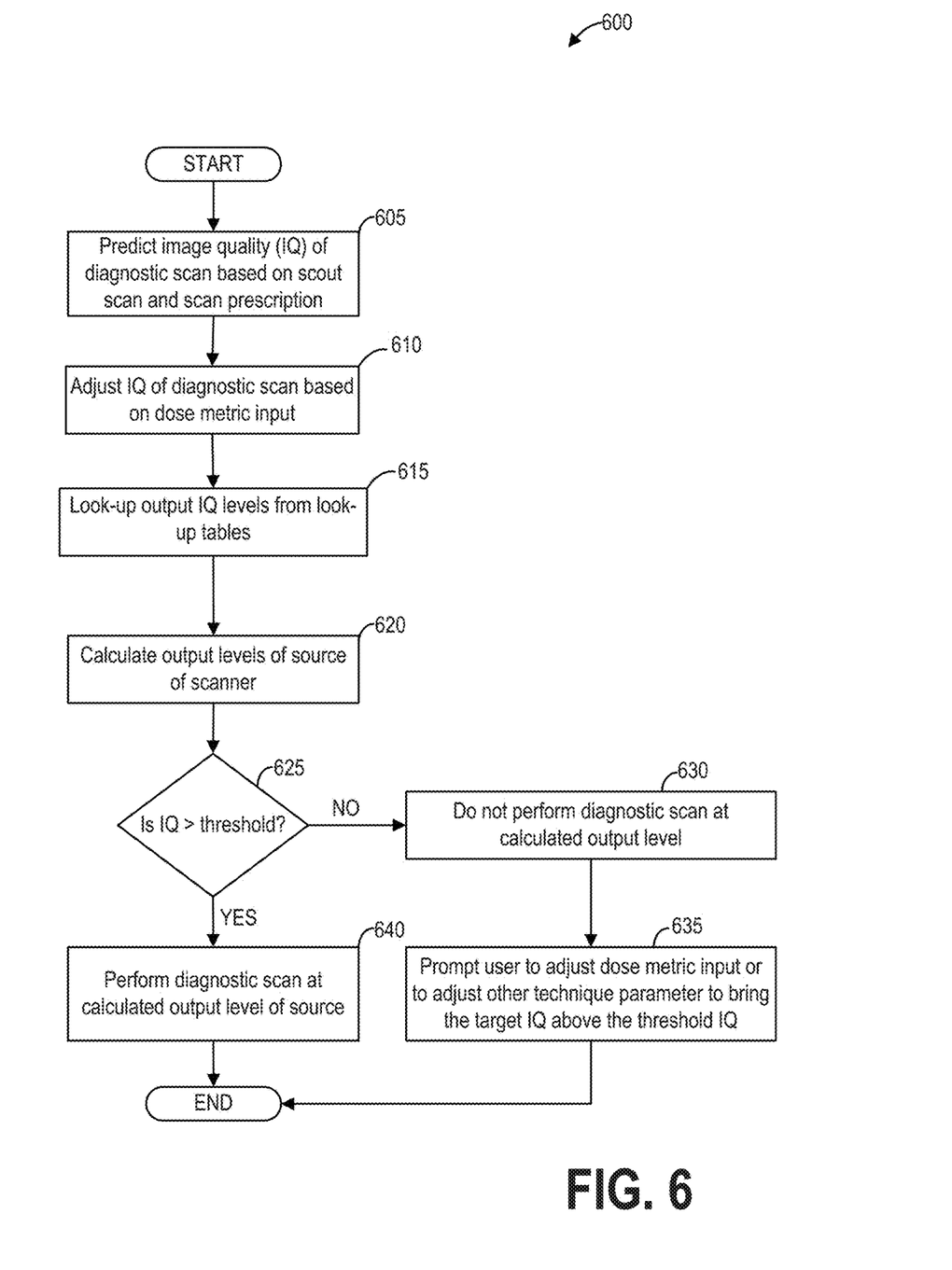
FIG. 6 shows a high-level flow chart illustrating an example method for determining parameters of a diagnostic scan based on the dose metric input received, and further predicting an image quality of the diagnostic scan based on the dose metric input.

Turning to FIG. 6, it illustrates an example method for determining parameters of a diagnostic scan based on the dose metric input received, and further predicting an image quality of the diagnostic scan based on the dose metric input. Specifically, method 600 includes predicting an IQ, and further includes performing the diagnostic scan at the predicted IQ, if the predicted IQ is higher than a threshold.

Method 600 may begin at 605. At 605, method 600 may include predicting IQ of the diagnostic scan. Herein, predicting IQ may further include predicting IQ based on scout scan and scan prescription. Next method 600 proceeds to 610, where the IQ may be adjusted based on dose metric input received at 520 of method 500, for example. Adjusting IQ based on the dose metric input may further include looking up IQ levels from look-up tables for the input dose value at 615.

Next, method 600 proceeds to 620, where output levels of the x-ray source may be calculated based on the predicted IQ. Then, method 600 proceeds to 625, where it may be determined if the predicted IQ is higher than a threshold. In some examples, the threshold may be an estimate of IQ below which the diagnostic scan may be compromised. In some more examples, the threshold may a range of acceptable IQ values, and if the predicted IQ is outside the range, it may be determined that the diagnostic scan may be compromised.

If the predicted IQ is below the threshold, then method 600 proceeds to 630 where the diagnostic scan may not be performed at the calculated output levels, and then method 600 proceeds to 635, where the user may be prompted to adjust the dose metric input or to adjust other technique parameter(s) to bring the target IQ above the threshold IQ, for example, and the method ends.

However, if the IQ is higher than the threshold when checked at 625, method 600 proceeds to 640, where the diagnostic scan may be performed at the calculated output level, and the method ends.

Figure 7:
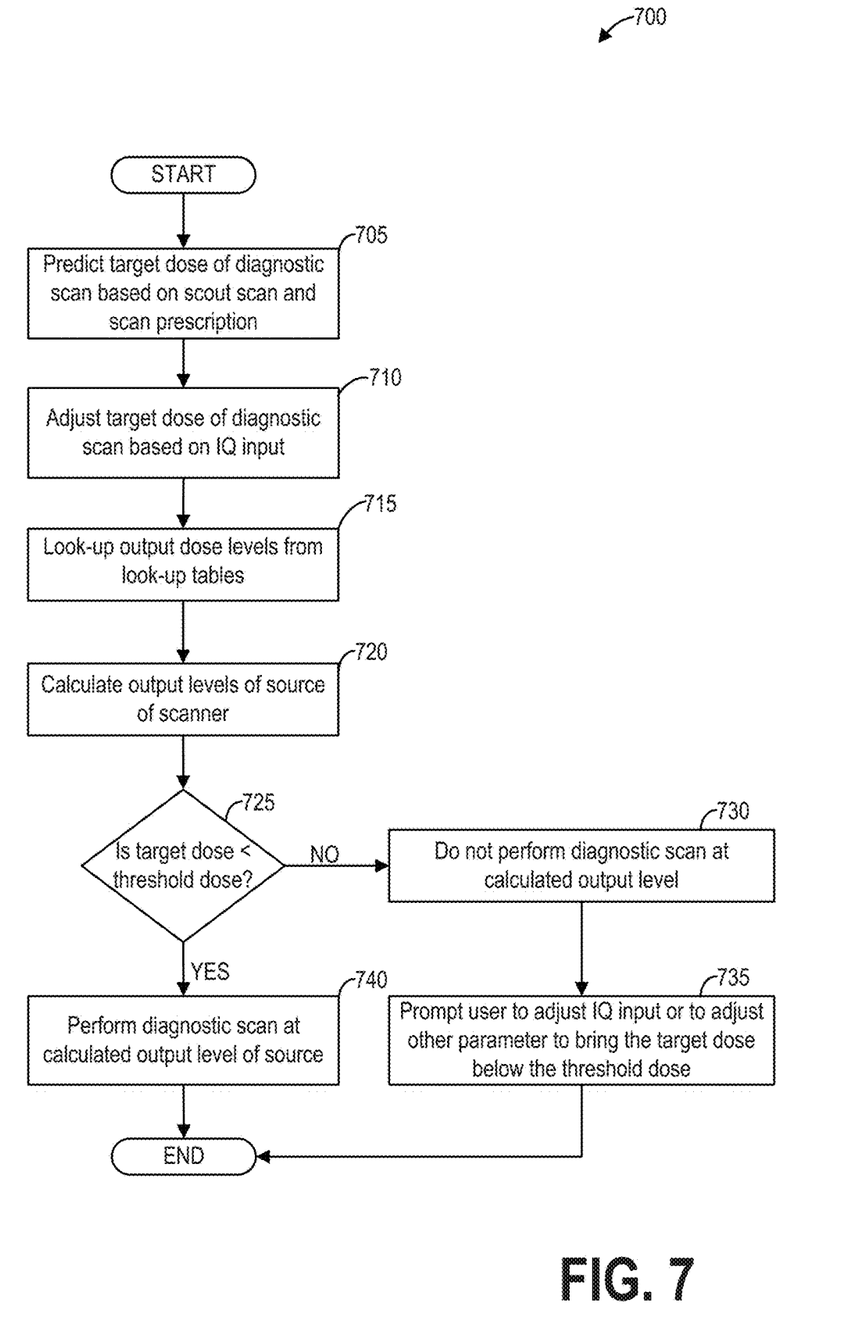
FIG. 7 shows a high-level flow chart illustrating an example method for determining the parameters of the diagnostic scan based on the image quality input received, and further predicting a target dose of the diagnostic scan based on the dose metric input.

FIG. 7 illustrates an example method 700 for determining the parameters of the diagnostic scan based on the image quality input received, and further predicting a target dose of the diagnostic scan based on the dose metric input. Specifically, method 700 includes predicting a target dose, and further includes performing the diagnostic scan at the predicted target dose, if the predicted dose is lower than a threshold dose.

Method 700 may begin at 705. At 705, method 700 may include predicting target dose of the diagnostic scan. Herein, predicting target dose may further include predicting target dose based on scout scan and scan prescription. Next method 700 proceeds to 710, where the target dose may be adjusted based on IQ input received at 530 of method 500, for example. Adjusting target dose based on the IQ input may further include looking up dose levels from look-up tables for the input IQ value at 715.

Next, method 700 proceeds to 720, where output levels of the x-ray source may be calculated based on the target output dose. Then, method 700 proceeds to 725, where it may be determined if the predicted dose is lower than a threshold dose. In some examples, the threshold dose may be upper threshold of acceptable dose levels. In some more examples, the threshold may be a range of acceptable dose values, and if the predicted dose is outside the range, it may be determined that the diagnostic scan may be compromised.

In some more examples, the threshold may a range of acceptable IQ values, and if the predicted IQ is outside the range, it may be determined that the diagnostic scan may be compromised.

If the predicted target dose is higher than the threshold dose, then method 700 proceeds to 730 where the diagnostic scan may not be performed at the calculated output levels, and then method 700 proceeds to 735, where the user may be prompted to adjust the IQ input or to adjust other parameter(s) to bring the target dose below the threshold dose, for example, and the method ends.

However, if the target dose is lower than the threshold when checked at 725, method 700 proceeds to 740, where the diagnostic scan may be performed at the calculated output level, and the method ends. In this way, the output level of the x-ray source may be adjusted specifically for a patient based on user-prescribed inputs of dose or IQ.

Thus, an example method includes in response to an object-specific dose metric or dose selection input by a user using a user interface operably coupled to a scanner, predicting an image quality of a diagnostic scan based on the received dose selection input and calculating an output source exposure level of the scanner for the predicted image quality, and performing the diagnostic scan at the specified output source exposure level responsive to the image quality being higher than a threshold. Additionally or alternatively, the method may further include in response to receiving an image quality input by the user using the user interface, predicting a target dose based on the received image quality input and comprising calculating a second output source exposure level of the scanner for the predicted target dose, the image quality input established by the user or derived from user inputs or a prior study. Additionally or alternatively, the method may include performing the diagnostic scan at the second output source exposure level when the target dose is lower than a threshold dose. Additionally or alternatively, predicting the image quality may include predicting the image quality based on one or more of a scout scan of an object, and a scan prescription, and further adjusting the image quality based on output image quality levels looked up from look-up tables. Additionally or alternatively, predicting the target dose may include predicting the target dose based on one or more of the scout scan, and the scan prescription, and further adjusting the target dose based on target dose levels looked up from the look-up tables. Additionally or alternatively, the look-up tables may include output image quality values as a function of input dose values. Additionally or alternatively, the look-up tables may include the target dose levels as a function of tube exposure values. Additionally or alternatively, the method may further include determining a size, a shape and a water equivalent diameter of the object based on the scout scan. Additionally or alternatively, the scan prescription may include one or more of a scan duration, and an anatomical region being scanned. Additionally or alternatively, the dose selection input may include a dose estimate based on a size of the object.

A technical effect of this disclosure includes governing the x-ray tube output that appropriately exposes the patient for a given clinical imaging task based on patient-specific and patient-size related input dose metric.

The systems and methods described above provide for a method, the method comprising in response receiving a dose selection input by a user using a user interface operably coupled to a scanner, predicting an image quality of a diagnostic scan based on the received dose selection input and further calculating an output source exposure level of the scanner for the predicted image quality; and performing the diagnostic scan at the specified output source exposure level responsive to the image quality being higher than a threshold. In a first example, the method may additionally or alternatively include in response to receiving an image quality input by the user using the user interface, predicting a target dose based in the received image quality input and calculating a second output source exposure level of the scanner for the predicted target dose, the image quality input established by the user or derived from user inputs or a prior study. A second example of the method optionally includes the first example and further includes performing the diagnostic scan at the second output source exposure level when the target dose is lower than a threshold dose. A third example of the method optionally includes one or more of the first and the second examples, and further includes predicting the image quality includes predicting the image quality based on one or more of a scout scan of an object, and a scan prescription, and further adjusting the image quality based on output image quality levels looked up from look-up tables. A fourth example of the method optionally includes one or more of the first through the third examples, and further includes wherein predicting the target dose includes predicting the target dose based on one or more of the scout scan, and the scan prescription, and further adjusting the target dose based on target dose levels looked up from the look-up tables. A fifth example of the method optionally includes one or more of the first through the fourth examples, and further includes wherein the look-up tables include output image quality values as a function of input dose values. A sixth example of the method optionally includes one or more of the first through the fifth example, and further includes wherein the look-up tables include the target dose levels as a function of tube exposure values. A seventh example of the method, the method may optionally include one or more of the first through the sixth example, and further includes determining a size, a shape and a water equivalent diameter of the object based on the scout scan. An eighth example of the method, the method may optionally include one or more of the first through the seventh example, and further includes wherein the scan prescription includes one or more of a scan duration, and an anatomical region being scanned. A ninth example of the method, the method may optionally include one or more of the first through the eighth example, and further includes wherein the dose selection input includes a dose estimate based on a size of the object.

The systems and methods described above provide for a method for automatic exposure control, the method comprising deriving a level of exposure of an x-ray source of a scanner for a diagnostic scan using patient information and information of an anatomical region being scanned, and further adjusting the level of exposure based on a user-prescribed input entered by a user using an user interface operably coupled to the scanner, the input being one of a desired image quality, and a desired dose target. In a first example, the method may additionally or alternatively include wherein the adjusting further includes calculating an output dose target based on one or more of the desired image quality, a volume computed tomography dose index, and a water equivalent diameter. A second example of the method optionally includes the first example and further includes wherein the adjusting further includes displaying the output dose target on the user interface, and performing the diagnostic scan when the output dose target is within a threshold dose. A third example of the method optionally includes one or more of the first and the second examples, and further includes calculating an output image quality based on one or more of the desired dose target, a volume computed tomography dose index, and a water equivalent diameter. A fourth example of the method optionally includes one or more of the first through the third examples, and further includes displaying the output image quality on the user interface, and performing the diagnostic scan when the output image quality is within a threshold level.

The systems and methods described above also provide for a system, the system comprising an x-ray source that emits a beam of x-rays toward an object to be imaged, an automatic exposure control (AEC) module operably connected to the source, and a processor operably coupled to the AEC module and configured with instructions in non-transitory memory that when executed cause the processor to: receive a dose input from a user via a user interface communicatively coupled to the AEC module and look up a first x-ray tube exposure based on the dose input; and predict a second x-ray tube exposure based on one or more of a clinical range selection, an object size, an object shape and a water equivalent diameter. In a first example of the system, the system may additionally or alternatively include wherein the processor includes further instructions for performing a diagnostic scan when a difference between the first x-ray tube exposure and the second x-ray tube exposure is lower than a threshold or within a dose range. A second example of the system optionally includes the first example and further includes wherein the processor is further configured to receive an image quality input from the user via the user interface of the AEC module and look up a first dose metric based on the image quality input, predict a second dose metric based on one or more of the clinical range selection, the object size, the object shape and the water equivalent diameter; and perform the diagnostic scan when difference between the first dose metric and the second does metric is lower than a threshold or within the dose range. A third example of the system optionally includes one or more of the first and the second examples and further includes wherein the clinical range selection includes a scan length, and an anatomical region being scanned. A fourth example of the system optionally includes one or more of the first through the third examples, and further includes wherein each of the object size, the object shape and the water equivalent diameter are determined based on a scout scan performed on the object.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
in response to receiving a dose selection input by a user via a user interface operably coupled to a computed tomography (CT) imaging system, predicting an image quality of a diagnostic scan based on the received dose selection;
calculating an output source exposure level of the CT imaging system for the predicted image quality; and
performing, via the CT imaging system, the diagnostic scan at the output source exposure level responsive to the image quality being higher than a threshold.

2. The method of claim 1, further comprising, in response to receiving an image quality selection input by the user via the user interface, predicting a target dose based on the received image quality selection and calculating a second output source exposure level of the CT imaging system for the predicted target dose, the image quality selection established by the user or derived from user inputs or a prior study.

3. The method of claim 2, further comprising performing the diagnostic scan at the second output source exposure level when the target dose is lower than a threshold dose.

4. The method of claim 3, wherein predicting the image quality includes predicting the image quality based on one or more of a scout scan of an object and a scan prescription, and further adjusting the image quality based on output image quality levels retrieved from look-up tables.

5. The method of claim 4, wherein predicting the target dose includes predicting the target dose based on one or more of the scout scan, and the scan prescription, and further adjusting the target dose based on target dose levels looked up from the look-up tables.

6. The method of claim 5, wherein the look-up tables include output image quality values as a function of input dose values.

7. The method of claim 6, wherein the look-up tables include the target dose levels as a function of tube exposure values.

8. The method of claim 5, further comprising determining a shape and a size of the object based on the scout scan, the size and the shape based on a water-equivalent diameter of the object.

9. The method of claim 8, wherein the scan prescription includes one or more of a scan duration, and an anatomical region being scanned.

10. The method of claim 1, wherein the dose selection includes a dose estimate based on a size of an object.

11. A method for automatic exposure control, comprising:
deriving a level of exposure of an x-ray source of a CT imaging system for a diagnostic scan using patient information and information of an anatomical region being scanned;
predicting an image quality of the diagnostic scan based on the level of exposure;
receiving a user-prescribed desired dose target entered by a user via a user interface operably coupled to the CT imaging system;
adjusting the predicted image quality based on the desired dose target; and
adjusting the level of exposure based on the adjusted predicted image quality.

12. The method of claim 11, further comprising calculating an output dose target based on one or more of a desired image quality, a volume computed tomography dose index, and a water-equivalent diameter.

13. The method of claim 12, further comprising displaying the output dose target on the user interface, and performing the diagnostic scan when the output dose target is within a threshold dose.

14. The method of claim 11, further comprising calculating an output image quality based on one or more of the desired dose target, a volume computed tomography dose index, and a water-equivalent diameter.

15. The method of claim 14, further comprising displaying the output image quality on the user interface, and performing the diagnostic scan when the output image quality is within a threshold level.

16. A system, comprising:
an x-ray source that emits a beam of x-rays toward an object to be imaged;
an automatic exposure control (AEC) module operably connected to the source; and
a processor operably coupled to the AEC module and configured with instructions in non-transitory memory that when executed cause the processor to:
receive a dose input from a user via a user interface communicatively coupled to the AEC module;
look up a first x-ray tube exposure based on the dose input; and
predict a second x-ray tube exposure based on one or more of a clinical range selection, an object size, an object shape, and a water-equivalent diameter.

17. The system of claim 16, wherein the processor includes further instructions for performing a diagnostic scan when a difference between the first x-ray tube exposure and the second x-ray tube exposure is lower than a threshold or within a dose range.

18. The system of claim 17, wherein the processor is further configured to:

receive an image quality input from the user via the user interface of the AEC module and look up a first dose metric based on the image quality input, predict a second dose metric based on one or more of the clinical range selection, the object size, the object shape, and the water-equivalent diameter; and perform the diagnostic scan when a difference between the first dose metric and the second dose metric is lower than a threshold or within the dose range.

19. The system of claim 18, wherein the clinical range selection includes a scan length, and an anatomical region being scanned.

20. The system of claim 18, wherein each of the object size, the object shape, and the water-equivalent diameter are determined based on a scout scan performed on the object.

* * * * *